United States Patent
Yan et al.

(10) Patent No.: US 11,433,087 B2
(45) Date of Patent: Sep. 6, 2022

(54) ANTI-TUMOR COMPOUND WITH HIGH CD169 AFFINITY, METHOD THEREOF, AND USE THEREOF

(71) Applicant: Xiamen Nuokangde Biological Technology Co., Ltd., Fujian (CN)

(72) Inventors: Xu Yan, Fujian (CN); Xuchun Han, Fujian (CN); Xianwu Wang, Fujian (CN)

(73) Assignee: Xiamen Nuokangde Biological Technology Co., Ltd., Fujian (CN)

( * ) Notice: Subject to any disclaimer, the term of this patent is extended or adjusted under 35 U.S.C. 154(b) by 85 days.

(21) Appl. No.: 16/847,770

(22) Filed: Apr. 14, 2020

(65) Prior Publication Data
US 2020/0237797 A1    Jul. 30, 2020

Related U.S. Application Data

(63) Continuation of application No. PCT/CN2018/103238, filed on Aug. 30, 2018.

(30) Foreign Application Priority Data

Oct. 14, 2017 (CN) .......................... 201710955544.7

(51) Int. Cl.
*A61K 31/7048*   (2006.01)
*A61P 35/00*   (2006.01)

(52) U.S. Cl.
CPC .......... *A61K 31/7048* (2013.01); *A61P 35/00* (2018.01)

(58) Field of Classification Search
CPC .... A61P 35/00; C07D 495/04; A61K 31/7048
USPC ........................................................ 514/23
See application file for complete search history.

(56) References Cited

FOREIGN PATENT DOCUMENTS

| CN | 1656113 A | 8/2005 |
|---|---|---|
| CN | 103819515 A | 5/2014 |
| CN | 105017340 A | 11/2015 |
| CN | 107501291 A | 12/2017 |
| CN | 107998140 A | 5/2018 |
| CN | 108047282 A | 5/2018 |

OTHER PUBLICATIONS

Int. Search Report cited in Application No. 2017109555447 dated Oct. 14, 2017, 6 pgs.
Int. Written Opinion cited in Application No. PCT/CN2018/103238 dated Dec. 6, 2018, 5 pgs.
"In Silico-Aided Design of a Glycan Ligand of Sialoadhesin for in Vivo Targeting of Macrophages", Sep. 11, 2012, Corwin M. Nycholat, Christoph Rademacher, Norihito Kawasaki and James C. Poulson, Journal of American Chemical Society, 4 pgs.
"Synthesis of 5-N- and 9_N-thioacylated sialic acids", Dec. 31, 1994, Rainer Isecke and Reinhard Brossmer, Science Direct, Tetrahedron, vol. 50, Issue 25, 16 pgs.
"CD22 Ligands on a Natural N-Glycan Scaffold Efficiently Deliver Toxins to B-Lymphoma Cells", Aug. 22, 2017, Wenjie Peng and James C. Paulson, Journal of American Chemical Society, 9 pgs.
"4H-Thieno[3,2-c]chromene based inhibitors of Notum Pectinacetylesterase", Jan. 18, 2016, Han Q, Pabba PK, Barbosa J., Babon R., Healy JP, Gardyan M2, Terranova KM, Brommage R, Thompson AY, Schmidt JM, Wildon AG, Xu X, Tarver JR Jr. and Cardon KG, Bioorganic & Medical Chemistry Letters, 4 pgs.
"Targeted delivery of lipid antigen to macrophases via the CD169/sialoadhesin endocytic pathway induces robust invariant natural killer T cell activation", May 2013, Norihito Kawasaki, Jose Luis Vela, Corwin M. Nycholat, Christoph Rademacher, Archana Khurane, Nico Van Rooijen, Paul R. Crocker, Mitchell Kronenberg and James C. Paulson, PNAS, vol. 110, No. 19, 6 pgs.

*Primary Examiner* — Shaojia A Jiang
*Assistant Examiner* — Michael C Henry
(74) *Attorney, Agent, or Firm* — Cooper Legal Group, LLC (57) ABSTRACT

The disclosure provides a CD169 high affinity anti-tumor compound (TCC-Neu5A) and its preparation and application. The CD169 high affinity anti-tumor compound is a small molecule compound, which has specific and broad-spectrum tumor killing characteristics. TCC-Neu5Ac could targets tumor cells in vivo and metabolize onto a surface of the tumor cells to form CD169 ligands. These tumor cells are recognized and phagocytized by CD169-positive macrophages, which then release tumor-related antigens and present them to other immune cells, triggering an anti-tumor immune response. The CD169 high affinity anti-tumor compound provided by the disclosure is effective for a variety of tumors and has an inhibitory effect on tumor metastasis. In addition, the CD169 high affinity anti-tumor compound provided by the disclosure can not only be injected but also be orally administered. Cytotoxicity and animal toxicity of the CD169 high affinity anti-tumor compound are very low.

18 Claims, 6 Drawing Sheets

Experimental group 1    Control group 1

Experimental group 2    Control group 2

ANTI-TUMOR COMPOUND WITH HIGH CD169 AFFINITY, METHOD THEREOF, AND USE THEREOF

RELATED APPLICATIONS

This application is a continuation of and claims priority to International Patent Application PCT/CN2018/103238, filed on Aug. 30, 2018, which claims priority to Chinese Patent Application 201710955544.7, filed on Oct. 14, 2017. International Patent Application PCT/CN2018/103238 and Chinese Patent Application 201710955544.7 are incorporated herein by reference.

FIELD OF THE INVENTION

The present disclosure relates to anti-tumor compounds, and more particularly, relates to an anti-tumor compound with high CD169 affinity, method thereof, and use thereof.

BACKGROUND OF THE INVENTION

Tumors are a severe threat to human health. Based on an understanding of tumor characteristics, people have studied how to kill tumors by various methods and have developed anti-tumor drugs. For example, due to the higher tumor metabolic strength relative to normal tissue, a variety of chemotherapy drugs have been developed. As another example, the use of tumor surface specific markers have been studied to develop monoclonal antibodies, such as Herceptin. In addition to the above methods of killing tumor directly, in recent years, people have begun to use immune checkpoint inhibitors to activate the body's autoimmune system in anti-tumor research, such as various antibodies and small molecule inhibitors targeting PD1, PDL-1, etc., which have achieved exciting results and are an important direction for anti-tumor research in the future.

Macrophages play an important role in the immune system. Macrophages can not only directly engulf tumor cells, but also transfer fragments of phagocytic tumor cells to other immune cells and activate the human autoimmune system to conduct anti-tumor reaction. Sialic acid binding immunoglobulin lectins (siglec) is a kind of lectin that can specifically bind sialic acid, mainly distributed on the surface of various immune cells. At present, there are 14 known siglec families. SIGLEC-1, also known as CD169, is mainly distributed on the surface of macrophages. SIGLEC-1 is highly homologous in mice and humans, so SIGLEC-1 can specifically bind to the n-acetylneuraminidase trisaccharide sequence (Neu5Acα2-3Galβ1-4GlcNAc). Neu5Ac represents N-acetylneuraminic acid, Gal represents galactose, GlcNAc represents N-acetylglucosamine, and α2-3 and β1-4 are a kind of chemical bond connection. However, SIGLEC1 has a weak affinity for binding to the natural sialidose ligands in nature.

People have been concerned about how to use macrophages to kill tumors.

SUMMARY OF THE INVENTION

In order to solve the problem of how to use macrophages for tumor treatment of the background technology, the present disclosure provides an anti-tumor compound with high CD169 affinity (TCC-Neu5Ac). A chemical structure of the anti-tumor compound is as follows:

or derivatives thereof.

The present disclosure further provides a method for preparing an anti-tumor compound with high CD169 affinity having a chemical structure of:

or derivatives thereof.

The method comprises:
1) mixing $^{TCC}$sia methyl ester, methanol, and NaOH solution, and stirring at room temperature to obtain a first mixture.
2) adding HCl aqueous solution into the first mixture, and adjusting a pH of the first mixture to 7 to obtain a second mixture.
3) removing a solvent of the second mixture, and purifying a first residue of the second mixture having the solvent removed to obtain a first solid. The first solid is the anti-tumor compound with high CD169 affinity.

In a preferred embodiment, in step 3, purifying the first residue of the second mixture having the solvent removed comprises purifying the first residue of the second mixture having the solvent removed by a column chromatography, and using $CH_2Cl_2$:MeOH=2:1 in the column chromatography.

In a preferred embodiment, a method for preparing the $^{TCC}$sia methyl ester in step 1 comprises:
S110) mixing $^{N3}$Sia methyl ester, palladium on carbon (Pd/C) catalyst, and anhydrous methanol to obtain a third mixture.
S120) adding acetyl chloride in the third mixture, and adjusting a pH of the third mixture to 1-2 to obtain a fourth mixture.
S130) stirring the fourth mixture in $H_2$ atmosphere until, when monitoring through thin layer chromatography, the fourth mixture is fully reacted to obtain a fifth mixture.
S140) filtering the fifth mixture to remove the Pd/C catalyst, and evaporating to remove a solvent to obtain a residual mixture.
S150) mixing the residual mixture, 1-ethyl-(3-dimethylaminopropyl) carbodiimide hydrochloride, 1-hydroxybenzotriazole, triethylamine, terminal complement complex carboxyl group (TCC-COOH), and dimethylformamide (DMF), and stirring in a dark environment to obtain a sixth mixture.
S160) evaporating the sixth mixture to remove a solvent of the sixth mixture, and purifying a second residue of the sixth mixture having the solvent removed by a second column chromatography to obtain a second solid. The second solid is the $^{TCC}$Sia methyl ester.

S170) in Step S160, using CH$_2$Cl$_2$:MeOH=10:1 in the second column chromatography.

In a preferred embodiment, a method for preparing the $^{N3}$Sia methyl ester comprises:

S210) adding sodium azide and $^{Tos}$Sia methyl ester into DMF to obtain a seventh mixture.

S220) heating the seventh mixture to 80° C., and further heating to remove a solvent of the seventh mixture.

S230) purifying a third residue of the seventh mixture having the solvent removed by a third column chromatography to obtain a third solid. The third solid is the $^{N3}$Sia methyl ester.

S240) in step S230, using EtOAc:MeOH=20:1 in the third column chromatography.

In a preferred embodiment, a method for preparing the $^{Tos}$Sia methyl ester comprises:

S310) mixing sialic acid, trifluoroacetic acid, and anhydrous methanol at the room temperature, and stirring until being clarified to obtain an eighth mixture.

S320) evaporating the eighth mixture to remove a solvent of the eighth mixture to obtain sialic acid methyl ester solid.

S330) drying the sialic acid methyl ester solid with P$_2$O$_5$ in vacuum to obtain a ninth mixture.

S340) evaporating the ninth mixture together with anhydrous pyridine to further remove water to obtain a tenth mixture.

S350) dissolving the tenth mixture in anhydrous pyridine, cooling to 0° C., and adding p-toluenesulfonyl chloride to obtain an eleventh mixture.

S360) heating the eleventh mixture to the room temperature, stirring, and heating under a reduced pressure to remove a solvent of the eleventh mixture.

S370) purifying a fourth residue of the eleventh mixture having the solvent removed by a fourth column chromatography to obtain a white solid. The white solid is the $^{Tos}$Sia methyl ester.

S380) in step S370, using EtOAc:MeOH=20:1 in the fourth column chromatography.

The present disclosure further provides a use of the anti-tumor compound with high CD169 affinity in a preparation of anti-tumor drugs.

The present disclosure further provides a method comprising using the anti-tumor compound with high CD169 affinity for treating a tumor.

The present disclosure provides an anti-tumor compound with high CD169 affinity, method thereof, and use thereof. The anti-tumor compound with high CD169 affinity of the present disclosure is 9-benzopyranothiophene-n-acetyl-neuraminic acid monosaccharide (TCC-Neu5Ac). The anti-tumor compound is a small molecule anti-tumor compound, which has specific and broad-spectrum tumor killing characteristics. TCC-Neu5Ac can target tumor tissue in vivo, metabolize onto the surfaces of tumor cells, and form CD169 ligand. After the tumor cells expressing TCC-Neu5Ac are recognized by macrophages nearby the tumors, the macrophages engulf the tumor cells, release tumor fragments, and present the tumor fragments to other immune cells, causing an anti-tumor immune response. The CD169 high affinity anti-tumor compound provided by the disclosure is effective for a variety of tumors and has an inhibitory effect on tumor metastasis. In addition, the CD169 high affinity anti-tumor compound provided by the disclosure can not only be injected but also orally administered. Cytotoxicity and animal toxicity of the anti-tumor compound with high CD169 affinity are very low, therefore resulting in the anti-tumor compound with high CD169 affinity having broad application prospect and market value.

BRIEF DESCRIPTION OF THE DRAWINGS

The present disclosure is further described with the combination of the accompanying drawings together with the embodiments. The accompanying drawings are some embodiments of the present disclosure. For those skilled in the art, it is possible to obtain other drawings according to the accompanying drawings without inventive labors.

DETAILED DESCRIPTION OF THE EMBODIMENTS

In order to further clarify technical objects, technical schemes, and technical advantages of the embodiments of the present disclosure, the present disclosure is further described with the combination of the accompanying drawings together with the embodiments. The embodiments are some embodiments of the present disclosure while not being all embodiments of the present disclosure. Thus, it is intended that the present disclosure cover other embodiments obtained by those skilled in the art without inventive labors.

The present disclosure provides an anti-tumor compound with high CD169 affinity, a structure of the anti-tumor compound is as follows:

The present disclosure provides a new small molecule anti-tumor compound, 9-benzopyranothiophene-n-acetyl-neuraminic acid monosaccharide (TCC-Neu5Ac). That is, the anti-tumor compound with high CD169 affinity has specific and broad spectrum characteristics for tumor killing. TCC-Neu5Ac is configured to target tumors in vivo and be metabolized onto surfaces of tumor cells of the tumors to obtain CD169 ligands. After the tumor cells are recognized by macrophages nearby the tumors, the macrophages phagocytose the tumor cells and release tumor fragments of the tumor cells to present the tumor fragments to other immune cells, resulting in an anti-tumor immune response. The anti-tumor compound with high CD169 affinity of the present disclosure is effective for a variety of tumors and has inhibitory effects on tumor metastasis. In addition, the anti-tumor compound with high CD169 affinity of the present disclosure is effective not only by injection but also by oral administration. Cytotoxicity and animal toxicity are very low, and it has a wide application prospect and market value.

The present disclosure also provides a method for preparing the anti-tumor compound with high CD169 affinity, comprising following steps:

1. Preparing TCC-COOH

1) At 0° C., dissolving 4-Chromanone in 15 mL dimethylformamide (N,N-dimethylformamide, also named as DMF), and adding phosphorus oxychloride (2.3 mL, 24.9 mmol) drop by drop to obtain a first mixture M51.

2) After stirring the first mixture M51 for 30 minutes at 0° C., heating to 80° C., maintaining for 1.5 hours, and then cooling to room temperature to obtain a second mixture M52.

3) After cooling the second mixture M52 to the room temperature, adding 1N NaOAc solution, after quenching, adding dichloromethane (2×25 mL), extracting to obtain an organic layer, concentrating the organic layer in vacuum to obtain a product, and then entering a next step without purifying.

4) At 0° C., dissolving the product in 30 mL ethanol solution in a 100 mL round-bottom flask, and adding ethyl 2-mercaptoacetate (2.73 mL, 24.9 mmol) and sodium ethoxide (21 wt %, in ethanol solution, 18.7 mL, 49.8 mmol) drop by drop to obtain a third mixture M53.

5) Heating the third mixture M53 to the room temperature, stirring overnight, filtering to obtain sediments, washing the sediments by water, and accumulating the sediments.

6) Adding the sediments to tetrahydrofuran (also named as THF) and 1N NaOH solution, and stirring 24 hours at 50° C. to obtain a fourth mixture M54.

7) Cooling the fourth mixture M54 to the room temperature, washing by $CH_2Cl_2$ (2×50 mL), adding 1N HCl, acidifying, filtering to obtain solid products, washing, and drying to obtain TCC-COOH.

A chemical structure of TCC-COOH is as follows:

In the method, a chemical reaction formula for a synthesis of TCC-COOH is as follows:

2. Preparing $^{Tos}$Sia Methyl Ester

1) Mixing sialic acid (15.0 g, 50 mmol), 1 mL trifluoroacetic acid, and 300 mL anhydrous methanol, and stirring at the room temperature until being clarified to obtain a fifth mixture M41. A chemical structure of the sialic acid is as follows:

2) Evaporating the fifth mixture to remove the solvent to obtain sialic acid methyl ester. The sialic acid methyl ester is a first white solid without being further purified;

3) Drying the first solid sialic acid methyl ester overnight in vacuum with $P_2O_5$ to obtain a sixth mixture M42;

4) Evaporating the sixth mixture M42 with anhydrous pyridine twice to remove trace water to obtain a seventh mixture M43;

5) After dissolving the seventh mixture M43 in 200 mL anhydrous pyridine, cooling to 0° C., and adding p-toluenesulfonyl chloride (10.0 g, 53 mmol) to obtain an eighth mixture M44;

6) Heating the eighth mixture M44 to the room temperature, stirring overnight, and heating under reduced pressure to remove the solvent to obtain a first residue; and 7) Purifying the first residue by column chromatography (EtOAc:MeOH=20:1) to obtain a second white solid (18.0 g, 38 mmol), which is the $^{Tos}$Sia methyl ester. A chemical structure of the $^{Tos}$Sia methyl ester is as follows:

3. Preparing N³Sia Methyl Ester

1) Adding 8.0 g sodium azide and the $^{Tos}$Sia methyl ester (14.0 g, 30 mmol) in 150 mL dimethylformamide (DMF) to obtain a ninth mixture M31;

2) Heating the ninth mixture M31 to 80° C., maintaining the ninth mixture M31 at 80° C. overnight, and then removing the solvent in vacuum to obtain a second residue; and 3) Purifying the second residue having the solvent removed by column chromatography (EtOAc:MeOH=20:1) to obtain a first solid, which is the N³Sia methyl ester. A chemical structure of the N³Sia methyl ester is as follows:

4. Preparing $^{TCC}$Sia Methyl Ester

1) Mixing the N³Sia methyl ester (3.0 g, 8.6 mmol), 300 mg Pd/C (palladium on carbon) catalyst, and 100 mL anhydrous methanol to obtain a tenth mixture M21;

2) Adding acetyl chloride in the tenth mixture M21, and adjusting a pH to 1-2 to obtain a eleventh mixture M22;

3) Stirring the eleventh mixture M22 in an atmosphere of hydrogen at the room temperature, and monitoring through thin layer chromatography (TLC) until being fully reacted to obtain a twelfth mixture M23. A duration of the monitoring is about 12 hours.

4) Filtering the twelfth mixture M23 to remove the Pd/C catalyst, and evaporating to remove the solvent to obtain a residual mixture M24;

5) Mixing the residual mixture M24, 1-ethyl-(3-dimethylaminopropyl) carbodiimide hydrochloride (EDC HCl) (2.0 g, 10.3 mmol), 1-hydroxybenzotriazole (HOBT) (1.4 g, 10.3 mmol, triethylamine (3.6 mL, 25.8 mmol), the TCC-COOH (2.0 g, 8.6 mmol), and 150 mL dimethylformamide (DMF), and stirring in a dark environment for 48 hours to obtain a thirteenth mixture M25; and 6) Evaporating the thirteenth mixture M25 to remove the solvent to obtain a third residue, and purifying the third residue having the solvent removed by a column chromatography (CH₂Cl₂:MeOH=10:1) to obtain a second solid (2.6 g, 4.8 mmol), which is the $^{TCC}$Sia methyl ester. A chemical structure of the $^{TCC}$Sia methyl ester is as follows:

5. Preparing Anti-Tumor Compounds with High CD169 Affinity (TCC-Neu5Ac)

1) Mixing the $^{TCC}$Sia methyl ester (536 mg, 1 mmol), 5 mL methanol, and 5 mL 2M NaOH solution, and stirring at the room temperature for 20 minutes to obtain a fourteenth mixture M11;

2) Adding 2M HCl aqueous solution in the fourteenth mixture M11, and adjusting a pH of the fourteenth mixture M11 to 7 to obtain a fifteenth mixture M12;

3) Removing a solvent of the fifteenth mixture M12 in vacuum to obtain a fourth residue, and purifying the fourth residue having the solvent removed through a column chromatography (CH₂Cl₂:MeOH=2:1) to obtain a light yellow solid (287 mg, 0.55 mmol), which is the anti-tumor compound with high CD169 affinity.

In particular, a chemical synthesis route of the anti-tumor compound with high CD169 affinity of the present disclosure is as follows:

The present disclosure also provides a use of the anti-tumor compound with high CD169 affinity.

The anti-tumor compound with high CD169 affinity of the present disclosure can achieve anti-tumor effects by injection or oral administration.

The anti-tumor effects of the anti-tumor compound with high CD169 affinity of the present disclosure is further described with experiments as follows.

Figure 1:
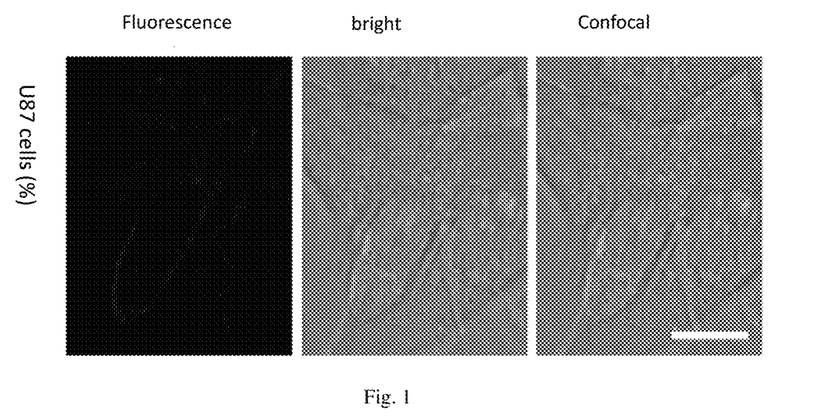
FIG. 1 shows a distribution graph of an anti-tumor compound with high CD169 affinity in a human malignant glioma cell line of Embodiment 1 of the present disclosure.

1. Distribution of the Anti-Tumor Compound with High CD169 Affinity of the Present Disclosure in a First Cell Line is as Follows:

Culturing human malignant glioma cells (U87) in a constant temperature incubator containing 5% $CO_2$ at 37° C., and a first medium of the human malignant glioma cells is a Dulbecco's Modified Eagle Medium (DMEM) comprising 10% fetal bovine serum;

Transferring the human malignant glioma cells to a first confocal cell culture dish, and culturing to a density of 50%;

Removing the first medium, adding a second medium comprising TCC-Neu5Ac with a concentration of 100 μmol (100 μM), and further culturing for 24 hours; and Removing the second medium comprising TCC-Neu5Ac, washing carefully with PBS for three times, adding a third medium, and observing a distribution of TCC-Neu5Ac in the human malignant glioma cells by a laser confocal microscope. An excitation light of the laser confocal microscope is 405 nanometers, and emitted light in a range of 420-480 nanometers is intercepted. FIG. 1 shows a distribution of TCC-Neu5Ac. It is found that TCC-Neu5Ac is distributed inside of the U87 cells and membranes of the U87 cells when observing in different fields of the laser confocal microscope.

Figure 2:
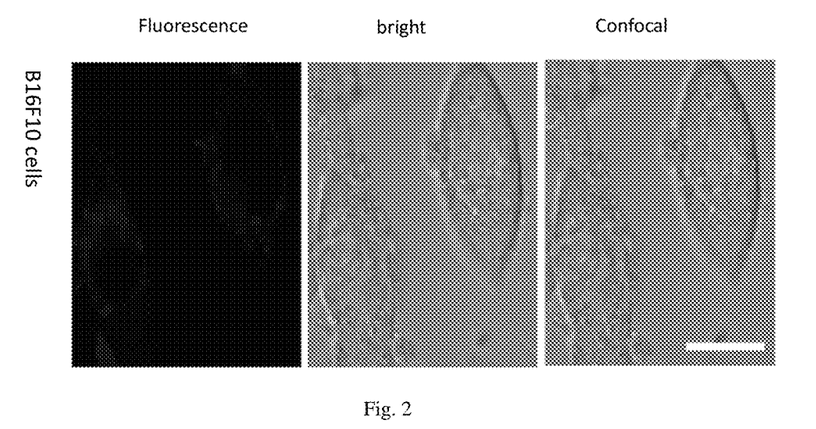
FIG. 2 shows a distribution graph of the anti-tumor compound with high CD169 affinity in a mouse melanoma cell line of Embodiment 1 of the present disclosure.

2. Distribution of the Anti-Tumor Compound with High CD169 Affinity of the Present Disclosure in a Second Cell Line is as Follows:

Culturing mouse melanoma cells (B16F10) in a constant temperature incubator containing 5% $CO_2$ at 37° C. A fourth medium of the mouse melanoma cells is a DMEM containing 10% fetal bovine serum;

Transferring the mouse melanoma cells to a second confocal cell culture dish, and culturing to a density of 50%;

Removing the fourth medium, adding a fifth medium comprising TCC-Neu5Ac with a concentration of 100 μmol (100 μM), and further culturing for 24 hours; and Removing the fifth medium comprising TCC-Neu5Ac, washing with PBS carefully for three times, adding a sixth medium, and observing a distribution of TCC-Neu5Ac in the mouse melanoma cells with the laser confocal microscope. The excitation light of the mouse melanoma cells is 405 nanometers, and emitted light in the range of 420-480 nanometers is intercepted. FIG. 2 shows a distribution of TCC-Neu5Ac. It is found that TCC-Neu5Ac is distributed inside of the B16F10 cells and cell membranes of the B16F10 cells when observing in different fields of the laser confocal microscope.

Figure 3:
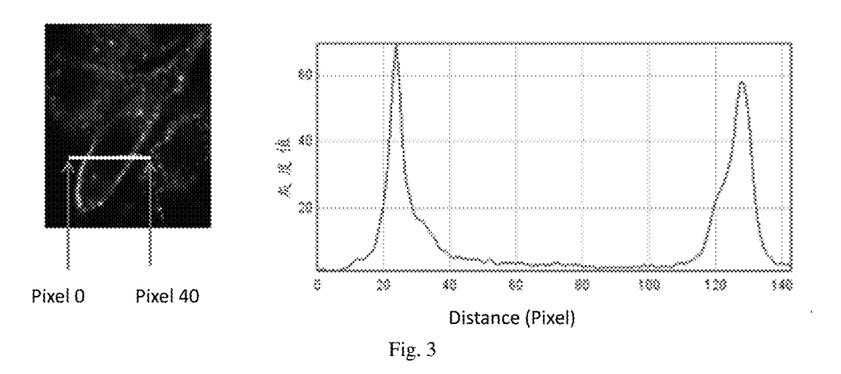
FIG. 3 shows a distribution analysis graph of the anti-tumor compound with high CD169 affinity in the mouse melanoma cell line of Embodiment 1 of the present disclosure.

3. Analyzing the Distribution of the Anti-Tumor Compound with High CD169 Affinity of the Present Disclosure Software in Cells (in this Embodiment, the Cells Comprise the Human Malignant Glioma Cells and the Mouse Melanoma Cells) by Software When being observed through the laser confocal microscope, it is found that a distribution in each of the cells is similar in the present disclosure, and the anti-tumor compound with high CD169 affinity is distributed inside of the cells and cell membranes of the cells at the same time. In order to determine a distribution on cell surfaces of the cells, we analyzed the anti-tumor compound with high CD169 affinity by software. With the latest version of ImageJ software and a dot-plot analysis tool, B16F10 cell image analysis in a distribution experiment of the anti-tumor compound with high CD169 affinity in the second cell line (the mouse melanoma cells) was carried out to obtain an analysis graph. Ordinate represents gray value and abscissa represents distance. The analysis graph is shown in FIG. 3. It is found that pixel positions with higher gray values are on the cell membranes, and TCC-Neu5Ac is mainly distributed on the cell membranes.

4. Analyzing Toxicity of the Anti-Tumor Compound with High CD169 Affinity of the Present Disclosure in the Cells.

Culturing human malignant glioma cells (U87) in the constant temperature incubator containing 5% $CO_2$ at 37° C., and a seventh medium of the human malignant glioma cells is DMEM containing 10% fetal bovine serum;

Transferring the human malignant glioma cells to a confocal cell culture dish, culturing to a density of 50%, removing the seventh medium, adding an eighth medium comprising TCC-Neu5Ac of different concentrations from 0 to 100 μmol (100 μM), and further culturing for 24 hours; and Removing the eighth medium comprising TCC-Neu5Ac, washing carefully with PBS for three times, adding a ninth medium, and counting dead cells of the human malignant glioma cells.

Figure 4:
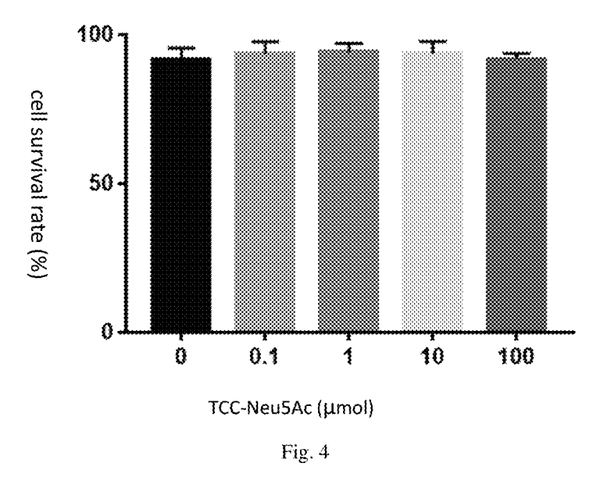
FIG. 4 shows an analysis graph of cell survival rate of the anti-tumor compound with high CD169 affinity comprising different concentrations of Embodiment 1 of the present disclosure.

Counting results of the dead cells are shown in FIG. 4, wherein abscissa represents different concentrations of TCC Neu5Ac in the eight medium, and ordinate represents a cell survival rate of the human malignant glioma cells. It is found from FIG. 4 that the cell survival rate of the human malignant glioma cells does not differ much when the eighth medium is added with TCC Neu5Ac with different concentrations (0-100 μmol). Therefore, the anti-tumor compound with high CD169 affinity of the present disclosure has extremely low toxicity in the cells and has potential ability for human tumor treatment.

5. Analyzing of Phagocytic Effects of Macrophages on Tumor Cells Cultured by the Anti-Tumor Compound with High CD169 Affinity of the Present Disclosure.

Figure 5:
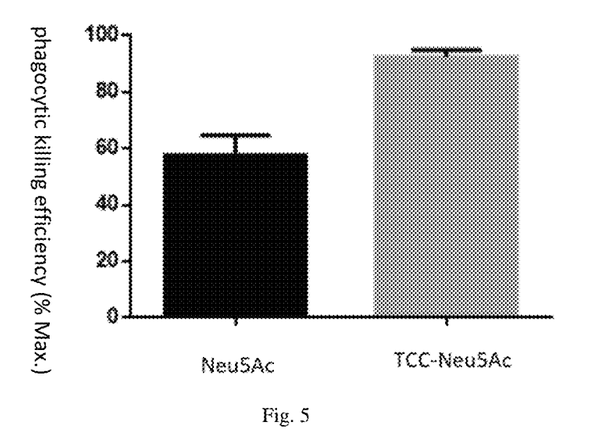
FIG. 5 shows an analysis graph of phagocytic effects of a macrophage cell line on a tumor cell line incubated by the anti-tumor compound with high CD169 affinity Embodiment 1 of the present disclosure.

Taking out bone marrow of 10 week old mice, adding with a solution of potassium ammonium chloride (ACK), and then culturing cells of the bone marrow in an Iscove's modified dulbecco medium (IMDM) comprising 10% (volume ratio) fetal bovine serum (FBS) and 10 ng/mL macrophage community stimulating factor to obtain bone marrow derived macrophages (BMDM). Culturing BMDM and B16F10 cells of a ratio of 5:1 respectively in an experimental group medium and a control group medium. Adding TCC-Neu5Ac to the experimental group medium, adding Neu5Ac of the same volume to the control group medium, detecting by Lactate dehydrogenase cytotoxicity test kit, selecting a 490 nm absorption peak in a microplate reader, and converting to phagocytic killing efficiency. Test results are shown in FIG. 5. It can be seen from FIG. 5 that a killing rate of phagocytes to tumors (in this embodiment, the tumors are the B16F10 cells) in the experimental group medium added with TCC-Neu5Ac is significantly higher than that in the control group medium added with Neu5Ac. It is found that a killing efficiency of phagocytes to the tumor cells cultured with the anti-tumor compounds with high CD169 affinity is higher than a killing efficiency of phagocytes to the tumor cells cultured with Neu5Ac.

6. Analyzing Anti-Tumor Effects in Mice Injected with the Anti-Tumor Compound with High CD169 Affinity of the Present Disclosure.

Figure 6:
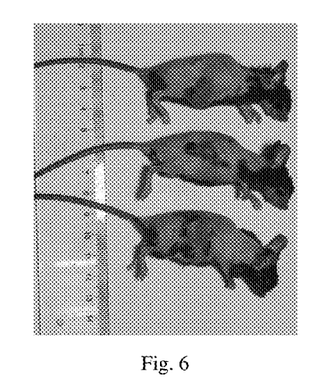
FIG. 6 shows a picture of an appearance of tumor-bearing mice injected with the anti-tumor compound with high CD169 affinity of Experimental group 1 of Embodiment 1 of the present disclosure.
Figure 7:
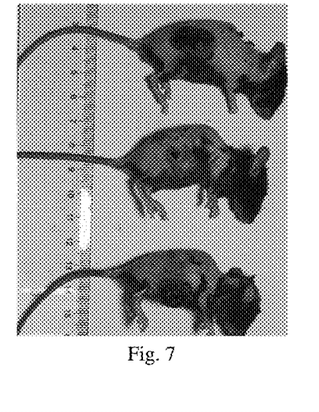
FIG. 7 shows a picture of an appearance of tumor-bearing mice injected with Phosphate-buffered saline (PBS) solution containing natural sialic acid in the same volume of Control group 1 of Embodiment 1 of the present disclosure.

Culturing B16F10 cells in a 10 cm cell culture dish to a density of 80%;

Digesting with 2 mL tyrisin for 90 seconds, neutralizing with 2 mL medium, centrifuging under 300 g for 3 minutes, rinsing with PBS repeatedly, centrifuging once to remove any remaining medium, and adding PBS to resuspend and count an amount of the B16F10 cells;

Injecting subcutaneously 1 million of the B16F10 cells into mice B6 (C57BL/6) for tumor planting, and then injecting 100 mL PBS comprising the anti-tumor compound of the present disclosure with a concentration of 100 μmol from a tail vein of mice every two days as an experimental group 1;

Injecting PBS of the same volume comprising 100 μmol natural sialic acid as a control group 1, and the other conditions of the control group 1 are the same as the experimental group 1; and After 15 days, removing hair from tumor areas of the mice, taking pictures (as shown in FIG. 6 and FIG. 7), taking out tumors from the mice, and taking pictures for analysis. Results are shown in FIG. 8.

FIG. 6 shows pictures of appearances of tumor-bearing mice injected with the anti-tumor compound with high CD169 affinity of the present disclosure of the experimental group 1. FIG. 7 shows pictures of appearances of tumor-bearing mice injected with PBS of the same volume comprising 100 μmol natural sialic acid of the control group 1. A left side of FIG. 8 shows the tumors taken from the tumor-bearing mice of the experimental group 1 injected with the anti-tumor compound with high CD169 affinity of the present disclosure, and a right side of FIG. 8 shows the tumors taken from the tumor-bearing mice of the control group 1.

Figure 8:
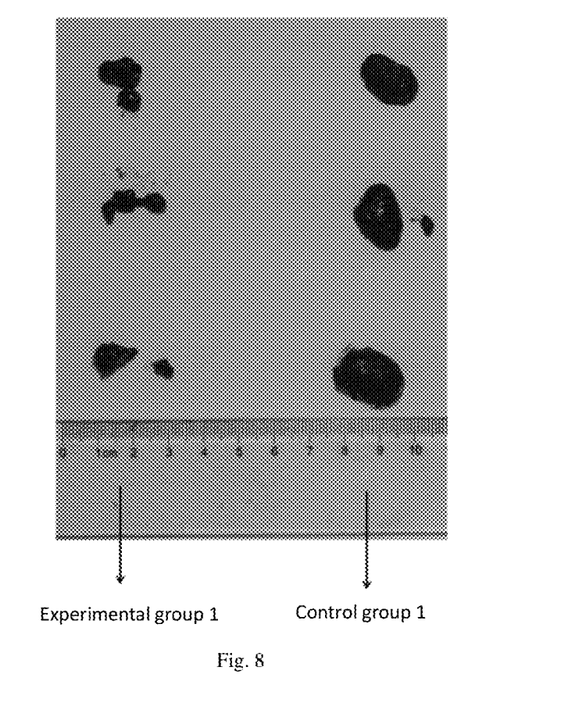
FIG. 8 shows a size comparison graph of tumors taken from mice in Experimental group 1 and Control group 1 of Embodiment 1 of the present disclosure.
Figure 9:
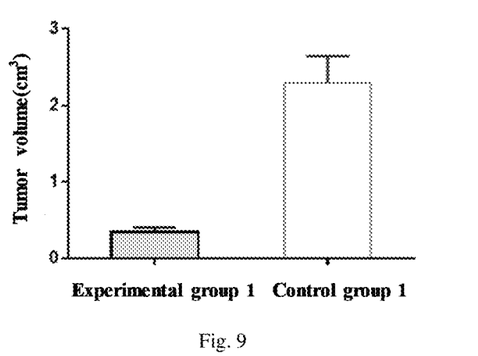
FIG. 9 shows a size comparison analysis graph of tumors taken from mice in Experimental group 1 and Control group 1 of Embodiment 1 of the present disclosure.

In addition, measuring sizes of the tumors of the experimental group 1 and the tumors of the control group 1, as shown in FIG. 8, and analyzing the sizes results in a data analysis diagram as shown in FIG. 9. As shown in FIG. 6 and FIG. 7, as well as a comparison of the sizes of the tumors on the left side and the right side in FIG. 8 and the data analysis diagram in FIG. 9, it is obvious that the sizes of the tumors of the tumor-bearing mice injected with the anti-tumor compound with high CD169 affinity of the present disclosure are significantly smaller than the sizes of the tumors of the tumor-bearing mice injected with PBS of the same volume comprising 100 μmol natural sialic acid. Therefore, it is found that the anti-tumor compound with high CD169 affinity of the present disclosure has remarkable anti-tumor effects.

7. Analyzing Anti-Tumor Effects in Mice Orally Administrated with the Anti-Tumor Compound with High CD169 Affinity of the Present Disclosure.

Culturing B16F10 cells in a 10 cm cell culture dish to a density of 80%, digesting with 2 mL tyrisin for 90 seconds, neutralizing with 2 mL medium, centrifuging under 300 g for 3 minutes, rinsing with PBS repeatedly, centrifuging once to remove any residual medium, adding PBS to resuspend and count an amount of the B16F10 cells, and injecting subcutaneously 1 million of the B16F10 cells into the of B6 mice (C57BL/6) for tumor planting;

Feeding 200 μL of an aqueous solution comprising the 100 μmol of the anti-tumor compound with high CD169 affinity of the present disclosure daily as an experimental group 2;

Feeding water solution with the same volume comprising natural sialic acid as a control group 2; and After 15 days, removing hair from tumor areas of the B6 mice, taking pictures, taking out tumors from the B6 mice, and taking pictures for analysis.

Figure 10:
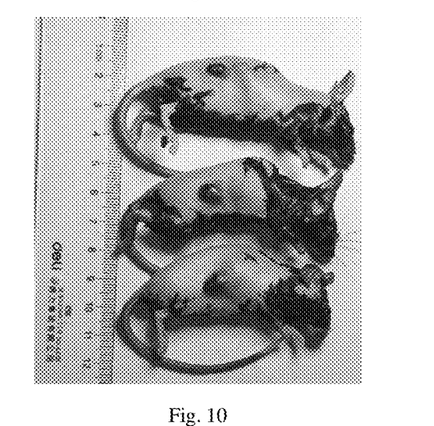
FIG. 10 shows a picture of an appearance of tumor-bearing mice orally administrated with the anti-tumor compound with high CD169 affinity of Experimental group 2 of Embodiment 1 of the present disclosure.
Figure 11:
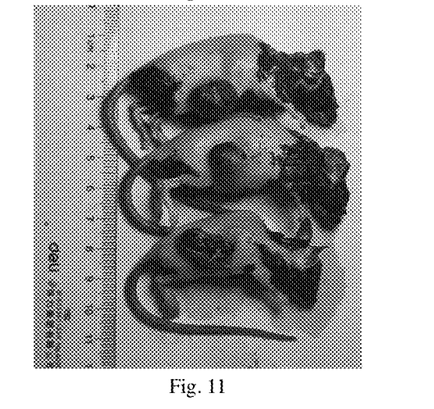
FIG. 11 shows a picture of an appearance of tumor-bearing mice orally administrated with PBS solution containing natural sialic acid in the same volume of Control group 2 of Embodiment 1 of the present disclosure.

FIG. 10 shows pictures of appearances of tumor-bearing mice of the experimental group 2 orally administrated with the anti-tumor compound with high CD169 affinity of the present disclosure. FIG. 11 shows pictures of appearances of tumor-bearing mice orally administrated with PBS of the same volume comprising 100 μmol natural sialic acid of the control group 2. A left side of FIG. 12 shows the tumors taken from the tumor-bearing mice of the experimental group 2 orally administrated with the anti-tumor compound with high CD169 affinity of the present disclosure, and a right side of FIG. 12 shows the tumors taken from the tumor-bearing mice of the control group 2.

Figure 12:
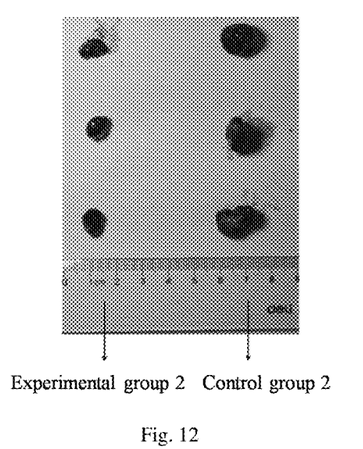
FIG. 12 shows a size comparison graph of tumors taken from mice in Experimental group 2 and Control group 2 of Embodiment 1 of the present disclosure.
Figure 13:
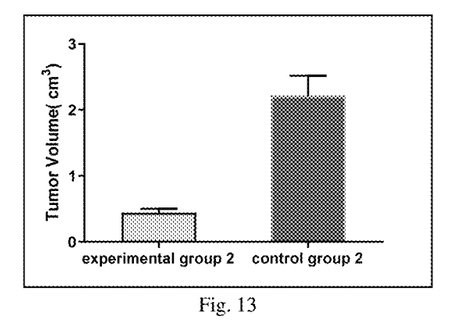
FIG. 13 shows a size comparison analysis graph of tumors taken from mice in Experimental group 2 and Control group 2 of Embodiment 1 of the present disclosure.

In addition, measuring sizes of the tumors of the experimental group 2 and the tumors of the control group 2, as shown in FIG. 12, and analyzing the sizes results in a data analysis diagram as shown in FIG. 13. As shown in FIG. 10 and FIG. 11, as well as a comparison of the sizes of the tumors in the left side and the right side of FIG. 12 and the data analysis diagram in FIG. 13, it is obvious that the sizes of the tumors of the tumor-bearing mice orally administrated with the anti-tumor compound with high CD169 affinity of the present disclosure are significantly smaller than the sizes of the tumors of the tumor-bearing mice orally administrated with PBS of the same volume comprising 100 μmol natural sialic acid (the PBS does not comprise the anti-tumor compound with high CD169 affinity of the present disclosure). Therefore, it is found that the anti-tumor compound with high CD169 affinity of the present disclosure has remarkable anti-tumor effects.

8. Analyzing Metastasis Effects of Tumors of Mice in the Present Disclosure.

Culturing B16F10 cells in a 10 cm cell culture dish to a density of 80%, digesting with 2 mL tyrisin for 90 seconds, neutralizing with 2 mL medium, centrifuging under 300 g for 3 minutes, rinsing with PBS repeatedly, centrifuging once to remove any residual medium, and adding PBS to resuspend and count an amount of the B16F10 cells.

Figure 14:
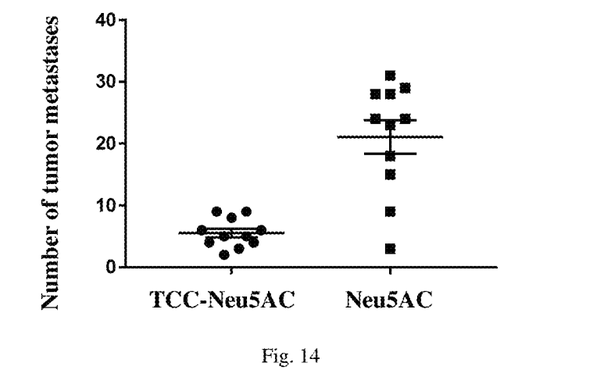
FIG. 14 shows an analysis graph of tumor metastasis effects of mice of Embodiment 1 of the present disclosure.

Injecting 1 million of the B16F10 cells into B6 mice (C57BL/6) from tail veins for preparing a tumor metastasis analysis model. Then, injecting 200 μL of an aqueous solution comprising the 100 μmol of the anti-tumor compound with high CD169 affinity of the present disclosure every two days from tail veins as an experimental group 3, and injecting water solution with the same volume comprising 100 μmol of natural sialic acid (Neu5Ac) as a control group 3. After 15 days, removing hair from tumor areas of the B6 mice and taking pictures. Then, taking out tumors from the B6 mice and taking pictures for analysis. An analysis graph of experimental data is shown in FIG. 14. An ordinate position of a black solid circle indicates a number of the tumors transferred to lungs of a mouse of the experimental group 3. An ordinate position of one black solid square indicates a number of the tumors transferred to lungs of a mouse of the control group 3. It can be seen from FIG. 14 that the number of the tumors transferred to the lungs in the experimental group 3 is far lower than that in the control group 3. Therefore, the anti-tumor compound with high CD169 affinity of the present disclosure has significant effects of inhibiting tumor metastasis.

9. Studying a Toxicity of the Anti-Tumor Compound with High CD169 Affinity of the Present Disclosure in Mice.

Figure 15:
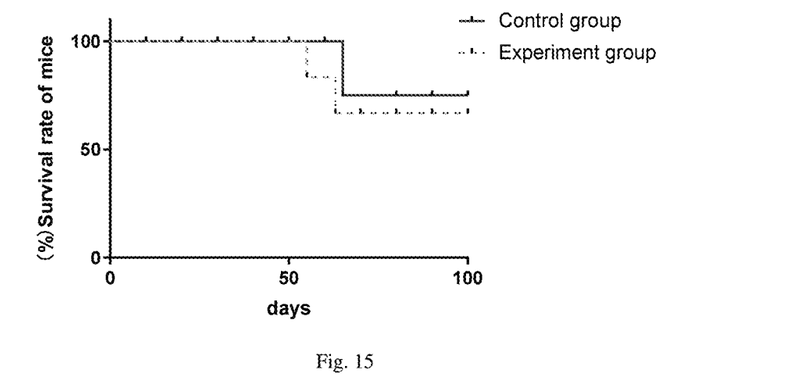
FIG. 15 shows a survival rate curve of mice in a toxicity study of mice of Embodiment 1 of the present disclosure.

Injecting a volume of 100 μL of PBS comprising 100 μmol concentration of the anti-tumor compound with high CD169 affinity of the present invention into B6 mice (C57BL/6) from tail veins every 5 days as experimental group 4, injecting natural sialic acid with the same volume and concentration as a control group 4, and observing and recording death of mice. Results are shown in FIG. 15. As shown in FIG. 15, abscissas represent a culture time of the mice, and ordinates represent a survival rate of the mice. It is found that the survival rate of the mice in the experimental group 4 and the control group 4 has little difference after culturing for 100 days. Therefore, the anti-tumor compound with high CD169 affinity of the present disclosure has very low toxicity to the mice and has potential ability for human tumor treatment.

It will be apparent to those skilled in the art that various modifications and variations can be made in the present disclosure without departing from the spirit or scope of the disclosure. Thus, it is intended that the present disclosure cover the modifications and variations of this disclosure provided they come within the scope of the appended claims and their equivalents.

What is claimed is:
1. An anti-tumor compound with high CD169 affinity, wherein the chemical structure of the anti-tumor compound is as follows:

2. A method for preparing an anti-tumor compound with high CD169 affinity having the chemical structure of:

wherein the method for preparing the anti-tumor compound with high CD169 affinity comprises:
1) mixing $^{Tcc}$sia methyl ester, methanol, and NaOH solution, and stirring at room temperature to obtain a first mixture,
2) adding HCl aqueous solution into the first mixture, and adjusting a pH of the first mixture to 7 to obtain a second mixture, and
3) removing a solvent of the second mixture, and purifying a first residue of the second mixture having the solvent removed to obtain a first solid, wherein the first solid is the anti-tumor compound with high CD169 affinity.

3. The method for preparing the anti-tumor compound with high CD169 affinity according to claim 2, wherein, in step 3, purifying the first residue of the second mixture having the solvent removed comprises:
purifying the first residue of the second mixture having the solvent removed by a column chromatography, and using $CH_2Cl_2$:MeOH=2:1 in the column chromatography.

4. The method for preparing the anti-tumor compound with high CD169 affinity according to claim 2, wherein a method for preparing the $^{Tcc}$sia methyl ester in step 1 comprises:

S110) mixing $^{N3}$Sia methyl ester, palladium on carbon (Pd/C) catalyst, and anhydrous methanol to obtain a third mixture,
S120) adding acetyl chloride in the third mixture, and adjusting a pH of the third mixture to 1-2 to obtain a fourth mixture,
S130) stirring the fourth mixture in $H_2$ atmosphere until, when monitoring through thin layer chromatography, the fourth mixture is fully reacted to obtain a fifth mixture,
S140) filtering the fifth mixture to remove the Pd/C catalyst, and evaporating to remove a solvent of the fifth mixture to obtain a residual mixture,
S150) mixing the residual mixture, 1-ethyl-(3-dimethyl-aminopropyl) carbodiimide hydrochloride, 1-hydroxy-benzotriazole, triethylamine, terminal complement complex carboxyl group (TCC-COOH), and dimethyl-formamide (DMF), and stirring in a dark environment to obtain a sixth mixture,
S160) evaporating the sixth mixture to remove a solvent of the sixth mixture, and purifying a second residue of the sixth mixture having the solvent removed by a second column chromatography to obtain a second solid, wherein the second solid is the $^{TCC}$Sia methyl ester, and
S170) in Step S160, using $CH_2Cl_2$:MeOH=10:1 in the second column chromatography.

5. The method for preparing the anti-tumor compound with high CD169 affinity according to claim 4, wherein a method for preparing the $^{N3}$Sia methyl ester comprises:
S210) adding sodium azide and $^{TOS}$Sia methyl ester into DMF to obtain a seventh mixture,
S220) heating the seventh mixture to 80° C., and further heating to remove a solvent of the seventh mixture,
S230) purifying a third residue of the seventh mixture having the solvent removed by a third column chromatography to obtain a third solid, wherein the third solid is the $^{N3}$Sia methyl ester, and
S240) in step S230, using EtOAc:MeOH=20:1 in the third column chromatography.

6. The method for preparing the anti-tumor compound with high CD169 affinity according to claim 5, wherein a method for preparing the $^{TOS}$Sia methyl ester comprises:
S310) mixing sialic acid, trifluoroacetic acid, and anhydrous methanol at the room temperature, and stirring until being clarified to obtain an eighth mixture,
S320) evaporating the eighth mixture to remove a solvent of the eighth mixture to obtain sialic acid methyl ester solid,
S330) drying the sialic acid methyl ester solid with $P_2O_5$ in vacuum to obtain a ninth mixture,
S340) evaporating the ninth mixture together with anhydrous pyridine to further remove water to obtain a tenth mixture,
S350) dissolving the tenth mixture in anhydrous pyridine, cooling to 0° C., and adding p-toluenesulfonyl chloride to obtain an eleventh mixture,
S360) heating the eleventh mixture to the room temperature, stirring, and heating under a reduced pressure to remove a solvent of the eleventh mixture,
S370) purifying a fourth residue of the eleventh mixture having the solvent removed by a fourth column chromatography to obtain a white solid, wherein the white solid is the $^{TOS}$sSia methyl ester, and
S380) in step S370, using EtOAc:MeOH=20:1 in the fourth column chromatography.

7. A method, comprising:
diluting the anti-tumor compound with high CD169 affinity according to claim 1 using a solution to obtain an anti-tumor drugs.

8. A method further, comprising:
diluting the anti-tumor compound with high CD169 affinity according to claim 2 using a solution to obtain an anti-tumor drugs.

9. A method further, comprising:
diluting the anti-tumor compound with high CD169 affinity according to claim 3 using a solution to obtain an anti-tumor drugs.

10. A method further, comprising:
diluting the anti-tumor compound with high CD169 affinity according to claim 4 using a solution to obtain an anti-tumor drugs.

11. A method further, comprising:
diluting the anti-tumor compound with high CD169 affinity according to claim 5 using a solution to obtain an anti-tumor drugs.

12. A method further, comprising:
diluting the anti-tumor compound with high CD169 affinity according to claim 6 using a solution to obtain an anti-tumor drugs.

13. A method, comprising:
at least one of injecting into a recipient or taking orally by the recipient the anti-tumor compound with high CD169 affinity according to claim 1 for treating a tumor.

14. A method, further comprising:
at least one of injecting into a recipient or taking orally by the recipient the anti-tumor compound with high CD169 affinity according to claim 2 for treating a tumor.

15. A method, further comprising:
at least one of injecting into a recipient or taking orally by the recipient the anti-tumor compound with high CD169 affinity according to claim 3 for treating a tumor.

16. A method, further comprising:
at least one of injecting into a recipient or taking orally by the recipient the anti-tumor compound with high CD169 affinity according to claim 4 for treating a tumor.

17. A method, further comprising:
at least one of injecting into a recipient or taking orally by the recipient the anti-tumor compound with high CD169 affinity according to claim 5 for treating a tumor.

18. A method, further comprising:
at least one of injecting into a recipient or taking orally by the recipient the anti-tumor compound with high CD169 affinity according to claim 6 for treating a tumor.

* * * * *